(12) United States Patent
Owoc

(10) Patent No.: US 9,468,645 B2
(45) Date of Patent: Oct. 18, 2016

(54) HIGHLY SOLUBLE PURINE BIOACTIVE COMPOUNDS AND COMPOSITIONS THEREOF

(71) Applicant: JHO Intellectual Property Holdings, LLC, Davie, FL (US)

(72) Inventor: Jack Owoc, Weston, FL (US)

( * ) Notice: Subject to any disclaimer, the term of this patent is extended or adjusted under 35 U.S.C. 154(b) by 3 days.

(21) Appl. No.: 14/628,626

(22) Filed: Feb. 23, 2015

(65) Prior Publication Data

US 2015/0238494 A1 Aug. 27, 2015

Related U.S. Application Data

(60) Provisional application No. 61/944,528, filed on Feb. 25, 2014.

(51) Int. Cl.

| | |
|---|---|
| *A61K 31/522* | (2006.01) |
| *A61K 45/06* | (2006.01) |
| *A23L 2/52* | (2006.01) |
| *A23L 2/02* | (2006.01) |
| *A23L 1/30* | (2006.01) |
| *A61K 9/00* | (2006.01) |
| *A61K 9/48* | (2006.01) |
| *A61K 31/00* | (2006.01) |

(52) U.S. Cl.
CPC ............... *A61K 31/522* (2013.01); *A23L 1/30* (2013.01); *A23L 2/02* (2013.01); *A23L 2/52* (2013.01); *A61K 9/0019* (2013.01); *A61K 9/0095* (2013.01); *A61K 9/4858* (2013.01); *A61K 31/00* (2013.01); *A61K 45/06* (2013.01); *A23V 2002/00* (2013.01)

(58) Field of Classification Search
CPC ............... A23V 2002/00; A23V 2200/31; A23V 2250/062; A23V 2250/21; A23V 2250/5108; A23V 2250/5118; A23V 2250/54246; A23V 2250/54252; A23V 2250/704; A23V 2250/712; A61K 31/522; A61K 2300/00; A61K 45/06; A61K 9/00
See application file for complete search history.

(56) References Cited

U.S. PATENT DOCUMENTS

| | | | | | |
|---|---|---|---|---|---|
| 837,282 | A | * | 12/1906 | Owoc | E01B 9/60 238/292 |
| 5,973,005 | A | * | 10/1999 | D'Amelio, Sr. | C07C 277/08 514/565 |
| 2006/0236421 | A1 | * | 10/2006 | Pennell | C12N 9/1007 800/278 |
| 2009/0257997 | A1 | * | 10/2009 | Owoc | A61K 9/0014 424/94.1 |

* cited by examiner

*Primary Examiner* — Debbie K Ware
(74) *Attorney, Agent, or Firm* — David W. Barman

(57) ABSTRACT

The invention provides nutritional supplements, in powder, tablet or capsule dosage forms and aqueous formulations, containing one or more of the purine bioactive compounds described including theacrine and theacrine species.

20 Claims, No Drawings

HIGHLY SOLUBLE PURINE BIOACTIVE COMPOUNDS AND COMPOSITIONS THEREOF

INDEX TO RELATED APPLICATIONS

This application is a non-provisional of, and claims benefit to U.S. Provisional Patent Application Ser. No. 61/944,528 filed Feb. 25, 2014 the disclosure of which is incorporated herein by reference in its entirety.

TECHNICAL FIELD

This disclosure of the present invention relates generally to new chemical entities (NCEs), which are a purine alkaloid compound structurally related to caffeine and abundantly present in Camellia kuchu, Camellia sinensis and several Coffea species. The disclosure relates more specifically to 1,3,7,9-tetramethyluric acid (theacrine), (O(2), 2-Methoxy-1,9-dimethyl-7H-purine-6,8-dione (liberine) and (O(2), 1,7,9-trimethyluric acid (methylliberine) wherein a basic uric acid structure has been partially or fully methylated in 2, 3 or 4 positions. This disclosure relates specifically to theacrine, and theacrine species such as liberine, and methylliberine and compositions thereof.

The disclosure of the present invention includes synthetic procedures of 1,3,7,9-tetramethyluric acid, O(2), 1,9-trimethyluric acid and O(2), 1,7,9-trimethyluric acid and their subsequent purification to yield compounds which are 99.9% pure and melting points of 228.9° C., 220° C. and 215° C. respectively.

The disclosure of the present invention further relates to compositions of matter wherein one or more of the purine alkaloid compounds is administered to mammals in combination with other psychostimulants including, but not limited to caffeine, theobromine, theophylline, yohimbine, combinations thereof, and other compounds known in the art to impart a psychostimulant effect.

In addition this disclosure of the present invention relates to nutritional supplements, in powder, tablet or capsule dosage forms, aqueous formulations, containing one or more of the purine bioactive compounds described.

In addition this disclosure of the present invention relates to nutritional supplements, in powder, tablet or capsule dosage forms, as solutions or suspensions, aqueous formulations, which may be used as stimulant of the central nervous system and metabolic stimulant. It may also be used medically to increase locomotor activity, increase, maintain and extend locomotor activity, enhance activity levels in a dose-dependent manner, reduce inflammation, reduce pain, increase endurance, reduce depression, impart a beneficial hypoglycemic effect and alleviate sleep deprivation.

BACKGROUND

Many stimulant nutritional supplements are available at various retail outlets, in many dosage forms, including tablets, capsules, powders, and liquids intended for human consumption. Most of them feature caffeine as the main stimulant. Theacrine offers the advantages of caffeine with the addition of the other benefits included in the summary below:

SUMMARY OF THE INVENTION

Some of the benefits of the present invention include:
Theacrine increases locomotor activity.
Theacrine) increases locomotor activity and maintains it for extended time.
Theacrine enhances activity levels in a dose-dependent manner.
Theacrine reduces inflammation.
Theacrine reduces pain.
Theacrine increases endurance.
Theacrine decreases depression.
Theacrine alleviates sleep deprivation.
During sleep deprivation with moderate-intensity exercise, theacrine supplementation may improve performance of complex central executive tasks.
Theacrine in combination with other psychostimulants has a synergistic effect that enhances the benefits described above.
Theacrine may impart a beneficial hypoglycemic effect in the management of hyperglycemia.

The synthesis of theacrine is achieved as follows: Theacrine is synthesized from uric acid by one step. At the presence of potassium carbonate, uric acid is methylated by trimethyl phosphate to give theacrine.

The one step pathway is depicted below:

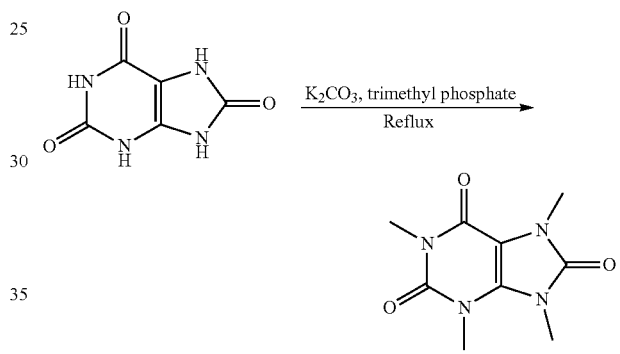

Stable aqueous compositions of matter useful for oral administration of at least one biologically-active form of a purine alkaloid compound structurally related to caffeine to a mammalian subject, which compositions comprise:
a) 1,3,7,9-tetramethyluric acid (theacrine), (O(2), 1,9-trimethyluric acid (ibertine) and (O(2), 1,7,9-trimethyluric acid (methylliberine) wherein a basic uric acid structure has been partially or fully methylated in 2, 3 or 4 positions
b) Water;
c) Water (pH range of 2.0-8.5); and
d) Aqueous buffer solutions (pH range: 1.5-9.0).

In one embodiment, the present invention provides stable aqueous compositions of matter useful for oral administration of at least one biologically-active form of a purine alkaloid compound structurally related to caffeine to a mammalian subject, which compositions comprise:
a) 1,3,7,9-tetramethyluric acid (theacrine), (O(2), 2-Methoxy-1,9-dimethyl-7H-purine-6,8-dione (liberine) and (O(2), 1,7,9-trimethyluric acid (methylliberine) wherein a basic uric acid structure has been partially or fully methylated in 2, 3 or 4 positions
b) Aqueous buffered solutions (pH range: 1.5-9.0).

In one embodiment, the composition provides said theacrine, or the theacrine species (as used, theacrine species includes liberine and methylliberine) are present in said aqueous composition in any amount between about 0.01% and about 10% by weight based on the total weight of said composition, including all percentages and ranges of percentages therebetween.

In one embodiment, the composition of the present invention is further comprising one or more nutritional adjuvant materials selected from the group consisting of: flavoring agents, colorants, viscosity modifiers, preservatives, fragrances, amino acids and their salts, vitamins, minerals, essential fatty acids, enzymes, co-enzymes, mono-glycerides, di-glycerides, tri-glyceride ester oils emulsifiers, hydrolyzed proteins, whey protein, stabilizers, flow modifiers, viscosity improvers, chelating agents, anti-oxidants, anti-microbials, benzoates, alcohols, esters of para-hydroxybenzoic acid, propionates, preservatives, surfactants (including anionic, cationic or nonionic surfactants) or combinations thereof.

In one embodiment, the composition of the present invention the total amount of said one or more nutritional adjuvant materials present is present in any amount between about 0.01% and about 10% by weight based on the total weight of said composition.

In one embodiment, the composition of the present invention is further comprising one or more natural beverages, including without limitation, milk products, soy products, ice cream, yoghurt, citrus fruit juices, non-citrus fruit juices, and vegetable juices, or components of any of the foregoing.

In one embodiment, the composition of the present invention has said one or more natural beverages is present in any amount between about 0.1% and about 99% by weight based on the total weight of said composition.

In one embodiment, the composition of the present invention is comprising an anti-microbial preservative present in an effective amount to inhibit microbial growth.

In one embodiment, the composition of the present invention comprises a preservative selected from the group consisting of: one or more esters of para-hydroxy benzoic acid, propionates, one or more sorbate salts, or combinations thereof.

The present invention also contemplates a method for administering a bioactive form of theacrine to a mammalian subject, said method comprising the steps of: preparing a composition according to the present invention; and orally administering the composition to said mammalian subject.

The present invention also contemplates a method for increasing locomotor activity in a mammalian subject, said method comprising the steps of: preparing a composition according to the present invention; and orally administering the composition to said mammalian subject.

The present invention also contemplates a method for increasing locomotor activity and maintaining for extended time this activity in a mammalian subject, said method comprising the steps of: preparing a composition according to the present invention; and orally administering the composition to said mammalian subject.

The present invention also contemplates a method for enhanced activity levels in a dose-dependent manner in a mammalian subject, said method comprising the steps of: preparing a composition according to the present invention; and orally administering the composition to said mammalian subject.

The present invention also contemplates a method for reducing inflammation in a mammalian subject, said method comprising the steps of: preparing a composition according to the present invention; and orally administering the composition to said mammalian subject.

The present invention also contemplates a method for reducing pain of a mammalian subject, said method comprising the steps of: preparing a composition according to the present invention; and orally administering the composition to said mammalian subject.

The present invention also contemplates a method for increasing endurance in a mammalian subject, said method comprising the steps of: preparing a composition according to the present invention; and orally administering the composition to said mammalian subject.

The present invention also contemplates a method for reducing depression in a mammalian subject, said method comprising the steps of: preparing a composition according to the present invention; and orally administering the composition to said mammalian subject.

The present invention also contemplates a method for alleviating the deleterious effects of hypergycemia in a mammalian subject, said method comprising the steps of: preparing a composition according to the present invention; and orally administering the composition to said mammalian subject.

The present invention also contemplates a method for alleviating the deleterious effects of sleep deprivation in a mammalian subject, said method comprising the steps of: preparing a composition according to the present invention; and orally administering the composition to said mammalian subject.

The present invention also contemplates a method in a mammalian subject, said method comprising the steps of: preparing a composition according to the present invention; and orally administering the composition to said mammalian subject wherein the administering is of one or more of purine alkaloids described herein in combination with other psychostimulants in any possible proportion in order to further enhance the benefits according to the methods of the present invention.

As contemplated herein, the method steps of orally administering, in one embodiment, further comprises the chronic administration of a composition according to a mammalian subject.

As contemplated herein, the method steps of orally administering, in one embodiment, further comprises the acute administration of a composition according to a mammalian subject.

The Table 1 below is data indicating assay results for stability of a theacrine solution prepared at 1.3 mg/ml and stored in USP Type I Glass vials for 15 weeks at RT and 40° C.

TABLE 1

Theacrine Stability Data

| | Initial | 1-wk | 2-wk | 4-wk | 8-wk | 15-wk |
|---|---|---|---|---|---|---|
| Storage: Room Temperature (RT) | | | | | | |
| Assay | 99.6 | 98.7 | 100.1 | 99.2 | 99.9 | 99.3 |
| Storage: 40 C. | | | | | | |
| Assay | 99.6 | 98.2 | 98.9 | 98.7 | 98.6 | 98.0 |

Table 2 below shows data indicating assay values of theacrine solutions at 0.1%, 0.2% and 0.4% stored in USP type I glass vials for 3 months at 40° C.

TABLE 2

| Theacrine Stability Data | | | | | |
|---|---|---|---|---|---|
| Storage: 40 C. | Initial | 10-d | 1-M | 2-M | 3-M |
| 0.1% Solution | 100.6 | 100.4 | 101 | 100.4 | 100.7 |
| 0.2% Solution | 99.8 | 98.6 | 98.9 | 97.5 | 99.4 |
| 0.4% Solution | 94.1 | 92.3 | 94.9 | 95.3 | 95.8 |

DETAILED DESCRIPTION OF THE PREFERRED EMBODIMENTS

The present invention provides aqueous compositions of matter suitable for oral administration to mammalian subjects, including without limitation humans, which compositions comprise theacrine species in solid or in liquid vehicles (carriers) that have been synthesized in commercial quantities by Vital Pharmaceuticals, Inc., d/b/a VPX/Redline of Davie, Fla.; theacrine itself has the general structure:

Structure I

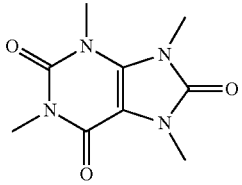

| Properties | |
|---|---|
| Molecular formula | $C_9H_{12}N_4O_3$ |
| Chemical name | 1,3,7,9-Tetramethyluric acid |
| Molar mass | 224.21 g/mol |
| CAS Registry Number | 2309-49-1 |

The material described by Structure I above, and the corresponding text in the description, including any and all of their derivative chemical forms, are all theacrine species and are, as such, the subject of the present disclosure.

Aqueous compositions of matter suitable for oral administration to mammalian subjects according to this disclosure may be caused to have any pH in the range of between about 1.5 and about 8.5 as desired, by adjusting such compositions using additions of appropriate amounts of strong or weak acids or bases including without limitation aqueous mineral acids including HCl, H3PO4, and bases including sodium hydroxide, ethanolamines, etc.

To prepare a composition according to one embodiment of the present invention, one may simply add a desired amount of theacrine to a selected volume of water, and sufficient stirring is affected to cause dissolution of the theacrine to afford an aqueous composition. Furthermore, according to one embodiment, the solution may be buffered before the addition of theacrine or the solution may be may be made more acidic or alkaline prior to the addition of theacrine. According to another embodiment, the total concentration of theacrine species in an aqueous solution provided hereby may be any amount between about 0.01% and about 20% (or more) by weight based on the total weight of the aqueous solution, including all percentages and ranges of percentages therebetween. According to another embodiment, the total concentration of theacrine in an aqueous solution provided hereby may be any amount between about 0.1% and about 20% by weight based on the total weight of the aqueous solution, including all percentages and ranges of percentages therebetween. According to another embodiment, the total concentration of theacrine species in an aqueous solution provided hereby may be any amount between about 0.1% and about 25% by weight based on the total weight of the aqueous solution, including all percentages and ranges of percentages therebetween. According to another embodiment, the total concentration of Theacrine species in an aqueous solution provided hereby may be any amount between about 0.1% and about 30% by weight based on the total weight of the aqueous solution, including all percentages and ranges of percentages therebetween. In an alternate embodiment, theacrine (or any one or more theacrine species) may be added to a natural beverage in any amount provided that an aqueous solution or suspension results.

In addition, a composition according to the present invention also includes nutritional adjuvant materials including flavoring agents, colorants, viscosity modifiers, preservatives, chelating agents, antioxidants, surface modifiers and other nutritional adjuvant materials. Other nutritional adjuvant materials include any substance which is generally recognized as promoting the health or function of a mammalian organism, including humans, or benefiting a composition useful thereof in terms of its efficacy, appearance, stability, consistency, aroma, or viscosity. Such substances include, but are not limited to, other amino acids and their salts, vitamins, minerals, essential fatty acids, enzymes, mono-glycerides, di-glycerides, tri-glyceride ester oils (including, for example vegetable oils and animal fats) emulsifiers, hydrolyzed proteins, whey protein, stabilizers, flow modifiers, viscosity improvers, chelating agents, enzymes, surfactants, whether anionic, cationic or nonionic, and combinations thereof. The total amount of the one or more nutritional adjuvant materials above present in a composition according to this disclosure is present in any amount between about 0.01% and about 50% by weight based on the total weight of said composition, including all percentages and ranges of percentages therebetween.

In addition to ingredients containing adjuvant materials, a composition according to one embodiment of the present invention also comprises one or more natural beverages. A natural beverage, as used herein, is a beverage suitable for human or animal consumption which contains the pulp, juice or any other constituent of a naturally-occurring fruit, vegetable, or animal product whether from the wild, cultured, cultivated on a farm or otherwise domesticated by Man. Natural beverages include without limitation materials including, but not limited to as milk products, soy products, ice cream, yoghurt, citrus fruit juices, non-citrus fruit juices, and vegetable juices, or components of any of the foregoing, wherein said natural beverages are present in any effective amount to impart flavor to the compositions, which are any amount between about 0.1% and about 99% by weight based on the total weight of said composition, including all percentages and ranges of percentages there between.

In addition to ingredients containing adjuvant materials, a composition according to one embodiment of the present invention comprises one or more synthetic beverages. A synthetic beverage is any beverage that is not a natural beverage.

In general, a composition according to one embodiment of the present invention is provided by combining and mixing the ingredients selected, including theacrine and any desired quantity of any one or more other ingredients specified herein. One advantage of compositions according to this disclosure is that they may be packaged at pH levels as low as about pH 2, in the cold or at about room temperature (alternative embodiment) or only slightly elevated temperature (alternative embodiment), as opposed to many prior art compositions which typically require hot packaging methods that utilize specialized and expensive equipment and packaging materials.

Thus, it is evident that a composition according to one embodiment of the present invention is made quite palatable by a mammalian subject, including human subjects desiring to administer theacrine orally in an aqueous mixture. Typical serving sizes may be any serving size in the range of about 1 milligram to about 50 grams, in an aqueous solution that is from about 20 ml to about 2500 ml in volume. The composition of theacrine in an aqueous composition according to this disclosure is limited only by the solubility limit of the theacrine and which may exceed 50 grams per liter and concentrations at or near the solubility limit are herein provided by contacting excess amounts of the theacrine in contact with water or an aqueous solution to provide a solution saturated with theacrine. Such saturated solutions may then be diluted slightly, to afford a concentrate from which other theacrine containing compositions may be conveniently provided.

Descriptions of Compositions

The following compositions are illustrative and not meant to limit the scope of the present invention.

1. An oral liquid composition (Ready-to-Drink) comprising Theacrine, said composition with a pH of about 2 to 8.5 being substantially stable at room temperature for normal warehouse storage conditions, stable at 104° F. (40 C. degrees) for shipping in hot weather trucks and/or overseas containers, and stable at 39° F. (4 C. degrees) in coolers so that it can be stored under refrigeration conditions. The composition comprising a suitable aqueous solvent or vehicle, a non-aqueous vehicle, a preservative, a physical stabilizing ingredient, one or more surfactants, and one or more buffer salts that can render the composition pH stable. The composition, in one embodiment contains psychostimulants, nucleotides, oligonucleotides, the monophosphates, diphosphates, triphosphates and cyclic derivatives of these nucleotides, and amino acids, vitamins and vitamin-like isoprenoids, peptides and one or more additional components selected from the group consisting of: lipids, starches, carbohydrates, polyols, minerals, electrolytes, amino trace elements, colorings, flavors, artificial sweeteners, and anti-oxidants.

2. An oral liquid composition for buccal sublingual administration comprising Theacrine, said composition with a pH of about 2 to 8.5 being substantially stable at room temperature for normal warehouse storage conditions, stable at 104° F. (40 C. degrees) for shipping in hot weather trucks and/or overseas containers, and stable at 39° F. (4 C. degrees) in coolers so that it can be stored under refrigeration conditions. The composition comprising a suitable aqueous solvent or vehicle, a non-aqueous vehicle, a preservative, a physical stabilizing ingredient, one or more surfactants, and one or more buffer salts that can render the composition pH stable. The composition, in one embodiment, contains psychostimulants, nucleotides, oligonucleotides, the monophosphates, diphosphates, triphosphates and cyclic derivatives of these nucleotides, and amino acids, vitamins and vitamin-like isoprenoids, peptides and one or more additional components selected from the group consisting of: lipids, starches, carbohydrates, polyols, minerals, electrolytes, amino trace elements, colorings, flavors, artificial sweeteners, and anti-oxidants.

3. An oral solid composition in the form of a capsule (LiCap®) with a liquid composition as fill material, said liquid fill material being substantially stable at room temperature for normal warehouse storage conditions, stable at 104° F. (40 C. degrees) for shipping in hot weather trucks and/or overseas containers, and stable at 39° F. (4 C. degrees) in coolers so that it can be stored under refrigeration conditions. The composition comprising a suitable lipophilic solvent or vehicle, a physical stabilizing ingredient, one or more surfactants, and one or more buffer salts that can render the composition pH stable. The composition in one embodiment, contains psychostimulants, nucleotides, oligonucleotides, the monophosphates, diphosphates, triphosphates and cyclic derivatives of these nucleotides, and amino acids, vitamins and vitamin-like isoprenoids, peptides and one or more additional components selected from the group consisting of: lipids, medium and short chain triglycerides, starches, polyols, carbohydrates, minerals, electrolytes, amino trace elements, colorings, and anti-oxidants.

4. An oral liquid composition containing from 1 gram to 100 grams of protein and from 1 g ram to 100 g of carbohydrates per serving comprising Theacrine, said liquid being substantially stable at room temperature for normal warehouse storage conditions, stable at 104° F. (40 C. degrees) for shipping in hot weather trucks and/or overseas containers, and stable at 39° F. (4 C. degrees) in coolers so that it can be stored under refrigeration conditions. The composition comprising an acid stable protein isolates, or a combination or blend of protein isolates, concentrates and hydrolyzates and caseins in micellar forms, a suitable aqueous solvent or vehicle, a non-aqueous vehicle, a preservative, a physical stabilizing ingredient, one or more surfactants, and one or more buffer salts that can render the composition pH stable. The composition, in one embodiment, contains psychostimulants, nucleotides, oligonucleotides, the monophosphates, diphosphates, triphosphates and cyclic derivatives of these nucleotides, and amino acids, vitamins and vitamin-like isoprenoids, peptides and one or more additional components selected from the group consisting of: lipids, starches, carbohydrates, polyols, minerals, electrolytes, amino trace elements, colorings, flavors, artificial sweeteners, and anti-oxidants.

5. An aqueous injectable composition for human consumption said composition being isotonic and sterile in nature comprising Theacrine, said injectable preparation with a pH of about 2, being substantially stable at room temperature for normal warehouse storage conditions, stable at 104° F. (40 C. degrees) for shipping in hot weather trucks and/or overseas containers, and stable at 39° F. (4 C. degrees) in coolers so that it can be stored under refrigeration conditions. The composition comprising a suitable aqueous solvent, a preservative, a physical stabilizing ingredient and one or more buffer salts that can render the composition pH stable. The composition, in one embodiment, contains psychostimulants, nucleotides, oligonucleotides, the monophosphates, diphosphates, triphosphates and cyclic derivatives of these nucleotides, and amino acids, peptides, proteins and carbohydrates.

6. An emulsion injectable composition for human consumption said composition being isotonic and sterile in nature comprising Theacrine, said injectable preparation with a pH of about 2, being substantially stable at room temperature for normal warehouse storage conditions, stable at 104° F. (40 C. degrees) for shipping in hot weather trucks and/or overseas containers, and stable at 39° F. (4 C. degrees in coolers so that it can be stored under refrigeration conditions. The composition comprising a suitable aqueous solvent, pharmaceutically acceptable oil (sesame, olive, castor, peanut, cotton seed, etc.), a natural emulsifier such as lecithin or any other synthetic emulsifier, be it of the polysorbate or ethoxylated glyceride type, a preservative, a physical stabilizing ingredient and one or more buffer salts that can render the composition pH stable. The composition, in one embodiment, contains psychostimulants, nucleotides, oligonucleotides, the monophosphates, diphosphates, triphosphates and cyclic derivatives of these nucleotides, and amino acids, peptides, proteins and carbohydrates.

EXAMPLES

Ready to Drink Formulation

Example I

| INGREDIENTS (Ready-to-Drink Formulation) | % w/w |
| --- | --- |
| Purified water | 97.1 |
| Theacrine | 1.00 |
| Caffeine | 2.00 |
| Gamma Butyrobetaine | 0.0156 |
| Glycerin | 1.067 |
| Anserine | 0.052 |
| Caffeine | 0.06 |
| Magnesium Tanshinoate | 0.0000009 |
| L-Leucine | 0.104 |
| L-Isoleucine | 0.052 |
| L-Valine | 0.0208 |
| 1,3-di-n-propyl-7-propargylxanthine | 1E−10 |
| Geranamine | 0.0004 |
| Citric acid to pH 3.33 | 0.179 |
| Sodium benzoate | 0.052 |
| Potassium sorbate | 0.01 |
| Bis picolinate vanadium | 0.0000002 |
| Salt | 0.005 |
| Potassium phosphate dibasic | 0.0206 |
| Sodium Erythorbate | 0.000001 |
| Nisaplin | 0.000001 |
| Sucralose | 0.073 |
| Malic acid | 0.083 |
| Flavor Melon | 0.105 |

Example II

| INGREDIENTS | % w/w |
| --- | --- |
| Theacrine | 2.10 |
| Caffeine | 4.20 |
| Peptides | 3.00 |
| AMP | 12.50 |
| UTP | 0.10 |
| Ubiquinone | 3.20 |
| Ethoxydiglycol | 20.0 |
| Alcohol USP | 50.0 |
| Benzyl alcohol | 1.00 |
| Buffer Salt(s) | QS to adjust pH |
| Purified Water | QS to 100 |

Example III

| INGREDIENTS | % w/w |
| --- | --- |
| Theacrine | 2.10 |
| Caffeine | 4.20 |
| Peptides | 3.00 |
| AMP | 12.50 |
| UTP | 0.10 |
| Ubiquinone | 3.20 |
| Propylene Glycol | 20.0 |
| Alcohol USP | 40.0 |
| Polysorbate 80 | 5.0 |
| Benzyl alcohol | 1.00 |
| Buffer Salt(s) | QS to adjust pH |
| Purified Water | QS to 100 |

Fill Material Composition for Capsule

Example I

| INGREDIENTS | % w/w |
| --- | --- |
| Theacrine | 2.10 |
| Medium chain triglyceride | 15.0 |
| Peptides | 3.00 |
| AMP | 12.50 |
| UTP | 0.10 |
| Ubiquinone | 3.30 |
| Oleic Acid | 52.0 |
| Purified Water | 1.0-10.0 |

Example II

| INGREDIENTS | % w/w |
| --- | --- |
| Theacrine | 2.10 |
| Peptides | 3.00 |
| AMP | 12.50 |
| UTP | 0.10 |
| Ubiquinone | 3.30 |
| Polysorbate 80 | 25.0 |
| PEG-40 Hydrogenated Castor Oil | 38.00 |
| PEG esters and monoglycerides | 15.0 |
| Purified Water | QS to 100 |

Example III

| INGREDIENTS | % w/w |
| --- | --- |
| Theacrine | 2.10 |
| Peptides | 3.00 |
| AMP | 12.50 |
| UTP | 0.10 |
| Ubiquinone | 3.30 |
| PEG-400 | 45.00 |
| PEG esters and monoglycerides | 9.00 |
| Polysorbate 80 | 20.0 |
| Buffer Salt(s) | QS to adjust pH |
| Purified Water | QS to 100 |

Medium Range pH RTD Protein Blend Formulations

| Ingredient | % w/w | Per 16 oz Serving |
|---|---|---|
| Theacrine | 1.00 | 2.10 |
| Whey Protein Isolate | 6.000 | 30.00 |
| Whey Protein Concentrate | 0.640 | 3.20 |
| Whey Hydrolysate | 0.320 | 1.60 |
| Micellar casein | 0.320 | 1.60 |
| Casein Protein Hydrolysate | 0.000 | 0.00 |
| Potassium Chloride | 0.076 | 0.38 |
| Ascorbic Acid | 0.012 | 0.06 |
| Vitamin E TPGS | 0.052 | 0.26 |
| Riboflavin 100 | 0.000 | 0.00000010 |
| Niacin | 0.000 | 0.0020 |
| Pyrodoxine HCl | 0.000 | 0.000007 |
| Calcium Panthothenate | 0.000 | 0.0011 |
| Magnesium Maleate | 0.020 | 0.1000 |
| d-ribose | 0.040 | 0.2000 |
| Centromix E | 0.600 | 3.00 |
| Saflower Oil | 1.200 | 6.00 |
| Sunflower Oil | 1.200 | 6.00 |
| Medium Chain Triglycerides | 0.800 | 4.00 |
| L-Glutamine | 0.025 | 0.13 |
| Glucose Polymers (Rice trin) | 0.800 | 4.00 |
| Waxy Maize Starch | 1.000 | 5.00 |
| High Amylose Starch (Amylose ADP11P) | 0.100 | 0.50 |
| Magnesium Citrate | 0.124 | 0.62 |
| Microcrystalline Cellulose | 0.100 | 0.50 |
| Malic Acid | 0.140 | 0.70 |
| Citric acid to pH 6.5 | 0.566 | 2.83 |
| Sodium Citrate to pH 6.5 | 0.140 | 0.70 |
| Sucralose | 0.011 | 0.06 |
| Glycerin | 3.000 | 15.00 |
| Na 2 EDTA | 0.050 | 0.25 |
| Sodium Benzoate | 0.090 | 0.45 |
| Potassium Sorbate | 0.190 | 0.95 |
| Water | QS | QS |

Low pH RTD Protein Formulations

| | Per 16 oz serving | % w/w |
|---|---|---|
| Theacrine | 2.10 | 0.25 |
| Whey Protein Isolate Acid Stable | 44.44 | 9.26 |
| Sucralose | 0.12 | 0.025 |
| Sodium EDTA | 0.24 | 0.050 |
| Potassium Sorbate | 0.96 | 0.200 |
| Sodium Benzoate | 0.48 | 0.100 |
| Citric Acid to pH 3.0 | QS | QS |
| Malic Acid to pH 3.0 | QS | QS |
| Water | 433.8 | 90.37 |
| | 480 | 100 |

Low pH RTD Protein Formulations

| | Per 16 oz serving | % w/w |
|---|---|---|
| Theacrine | 2.10 | 0.25 |
| Whey Protein Isolate Acid Stable | 44.44 | 9.26 |
| Sucralose | 0.12 | 0.025 |
| Waxy Maize Starch | 4.80 | 1.00 |
| Glucose Polymers (Rice trin) | 0.96 | 0.20 |
| Na EDTA | 0.24 | 0.050 |
| Potassium Sorbate | 0.96 | 0.200 |
| Sodium Benzoate | 0.48 | 0.100 |
| Citric Acid to pH 3.0 | QS | QS |
| Malic Acid to pH 3.0 | QS | QS |
| Water | QS | QS |
| TOTAL | 480 | 100 |

Aqueous Injectable Formulations

Example I

| Ingredient | % w/v |
|---|---|
| Theacrine | 6.25 |
| Caffeine | 12.5 |
| AMP | 12.5 |
| UTP | 0.10 |
| Amino Acids | 3.0-7.0 |
| Polysorbate 80 | 0.40 |
| Sodium CMC | 0.50 |
| Sodium Chloride | 0.90 |
| Benzyl alcohol | 0.90 |
| Buffer Salt(s) | QS to adjust to pH 3--6.5 |
| Sodium Hydroxide | QS to adjust to pH 3-6.5 |
| Water for Injection | QS to 100 |

Example II

| Ingredient | % w/v |
|---|---|
| Theacrine | 6.25 |
| Caffeine | 12.50 |
| UTP | 0.10 |
| Amino Acids | 3.0-7.0 |
| Polysorbate 80 | 0.40 |
| Sorbitol | 40.00 |
| Sodium Chloride | 0.90 |
| Benzyl alcohol | 0.90 |
| Buffer Sat(s) | QS to adjust to pH 3--6.5 |
| Sodium Hydroxide | QS to adjust to pH 3-6.5 |
| Water for Injection | QS to 100 |

Example III

| Ingredient | % w/v |
|---|---|
| Theacrine | 6.25 |
| Caffien | 12.5 |
| Polysorbate 80 | 0.40 |
| AMP | 12.50 |
| UTP | 0.10 |
| Amino Acids | 3.0-7.0 |
| Sodium Citrate | 0.50 |
| Sodium Chloride | 0.90 |
| Benzyl alcohol | 0.90 |
| Buffer Salt(s) | QS to adjust to pH 3--6.5 |
| Sodium Hydroxide | QS to adjust to pH 3-6.5 |
| Water for Injection | QS to 100 |

Emulsion Injectable Formulations

Example I

| Ingredient | % w/v |
|---|---|
| Theacrine | 6.25 |
| Caffeine | 12.5 |
| AMP | 12.5 |
| UTP | 0.10 |
| Amino Acids | 3.0-7.0 |
| Sesame Oil | 2.0-12.0 |

-continued

| Ingredient | % w/v |
| --- | --- |
| Polysorbate 80 | 0.40 |
| Sodium Chloride | 0.90 |
| Benzyl alcohol | 0.90 |
| Buffer Salt(s) | QS to adjust to pH 3--6.5 |
| Sodium Hydroxide | QS to adjust to pH 3-6.5 |
| Water for Injection | QS to 100 |

Example II

| Ingredient | % w/v |
| --- | --- |
| Theacrine | 6.25 |
| Caffeine | 12.5 |
| AMP | 12.50 |
| UTP | 0.10 |
| Amino Acids | 3.0-7.0 |
| Olive Oil | 1.0-15.0 |
| Lecithin | 0.50-5.0 |
| Sorbitol | 30.00 |
| Sodium Chloride | 0.90 |
| Benzyl alcohol | 0.90 |
| Buffer Sat(s) | QS to adjust to pH 3-6.5 |
| Sodium Hydroxide | QS to adjust to pH 3-6.5 |
| Water for Injection | QS to 100 |

Example III

| Ingredient | % w/v |
| --- | --- |
| Theacrine | 6.25 |
| Caffeine | 12.5 |
| Peanut Oil | 1.0-15.0 |
| Polysorbate 80 | 0.2-10.0 |
| AMP | 12.50 |
| UTP | 0.10 |
| Amino Acids | 3.0-7.0 |
| Sodium Citrate | 0.50 |
| Sodium Chloride | 0.90 |
| Benzyl alcohol | 0.90 |
| Buffer Salt(s) | QS to adjust to pH 3--6.5 |
| Sodium Hydroxide | QS to adjust to pH 3-6.5 |
| Water for Injection | QS to 100 |

A composition as provided herein may be administered chronically. As used herein, "chronically" has its normal meaning, which generally means repeated ingestion over a period of several days, several weeks or even several months. "Chronic" is generally not acute.

Consideration must be given to the fact that although this disclosure has been described and disclosed in relation to certain preferred embodiments, obvious equivalent modifications and alterations thereof will become apparent to one of ordinary skill in this art upon reading and understanding this specification and the claims appended hereto. This includes subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claims so modified. This also includes combination of the features and/or limitations of one or more of the independent claims with features and/or limitations of another independent claim to arrive at a modified independent claim, with the remaining dependent claims in their original text being read and applied to any independent claim so modified. Accordingly, the present disclosure is intended to cover all such modifications and alterations and is not intended to be necessarily limited by any one or more particular strict interpretations of the claims that now follow.

What is claimed is:

1. Stable aqueous compositions for oral administration of at least one biologically-active form of a purine alkaloid compound structurally related to caffeine to a mammalian subject, which compositions comprise:
    a) 1,3,7,9-tetramethyluric acid (theacrine), (O(2), 2-Methoxy-1,9-dimethyl-7H-purine-6,8-dione (liberine) and (O(2), 1,7,9-trimethyluric acid (methylliberine), said liberine and methylliberine collectively referred to as theacrine species, wherein a basic uric acid structure has been partially or fully methylated in 2, 3 or 4 positions; and
    b) at least one aqueous buffered solution having a pH range of about 1.5-9.0.

2. A composition according to claim 1 wherein said theacrine, or theacrine species are present in said aqueous composition in any amount between about 0.01% and about 10% by weight based on the total weight of said composition, including all percentages and ranges of percentages therebetween.

3. A composition according to claim 1, further comprising one or more nutritional adjuvant materials selected from the group consisting of: flavoring agents, colorants, viscosity modifiers, preservatives, fragrances, amino acids and their salts, vitamins, minerals, essential fatty acids, enzymes, co-enzymes, mono-glycerides, di-glycerides, tri-glyceride ester oils emulsifiers, hydrolyzed proteins, whey protein, stabilizers, flow modifiers, viscosity improvers, chelating agents, anti-oxidants, anti-microbials, benzoates, alcohols, esters of para-hydroxybenzoic acid, propionates, preservatives, surfactants, including anionic, cationic or nonionic surfactants, or combinations thereof.

4. A composition according to claim 3 wherein the total amount of said one or more nutritional adjuvant materials present is present in any amount between about 0.01% and about 10% by weight based on the total weight of said composition.

5. A composition according to claim 1 further comprising one or more natural beverages, including, milk products, soy products, ice cream, yoghurt, citrus fruit juices, non-citrus fruit juices, vegetable juices, components of any of the foregoing, or combinations thereof.

6. A composition according to claim 5 wherein said one or more natural beverages is present in any amount between about 0.1% and about 99% by weight based on the total weight of said composition.

7. A composition according to claim 1, comprising an anti-microbial preservative present in an effective amount to inhibit microbial growth.

8. A composition according to claim 7 wherein said preservative comprises a preservative selected from the group consisting of: one or more esters of para-hydroxy benzoic acid, propionates, and one or more sorbate salts.

9. A method for administering a bioactive form of theacrine to a mammalian subject said method comprising the steps of: preparing a composition according to claim 1; and orally administering said composition.

10. The method of claim 9 wherein said method further comprises increasing locomotor activity in the mammalian subject.

11. The method of claim 10, wherein said increasing locomotor activity is maintained for extended time by chronic oral administration of said composition to the mammalian subject.

12. The method of claim 9 further comprising providing enhanced activity levels in a dose-dependent manner in the mammalian subject.

13. The method of claim 9 further comprising reducing inflammation in the mammalian subject.

14. The method of claim 9 further comprising reducing pain of the mammalian subject.

15. The method of claim 9 further comprising increasing endurance in the mammalian subject.

16. The method of claim 9 further comprising reducing depression in the mammalian subject.

17. The method of claim 9 further comprising alleviating the deleterious effects of hypergycemia in the mammalian subject.

18. The method of claim 9 further comprising alleviating the deleterious effects of sleep deprivation in the mammalian subject.

19. The method of claim 9 further comprising administering one or more of purine alkaloids in combination with at least one psychostimulant.

20. The method of claim 9, wherein said step of orally administering comprises chronic or acute administration of a composition to the mammalian subject.

* * * * *